(12) United States Patent
Zhao et al.

(10) Patent No.: US 7,629,179 B2
(45) Date of Patent: Dec. 8, 2009

(54) SURFACES COATED WITH TARGET-INDUCED FLUORESCENT COMPOUNDS FOR DETECTION OF TARGET ELEMENTS

(75) Inventors: Xiaojun Julia Zhao, Grand Forks, ND (US); David T. Pierce, Grand Forks, ND (US)

(73) Assignee: University of North Dakota, Grand Forks, ND (US)

( * ) Notice: Subject to any disclaimer, the term of this patent is extended or adjusted under 35 U.S.C. 154(b) by 130 days.

(21) Appl. No.: 11/368,315

(22) Filed: Mar. 3, 2006

(65) Prior Publication Data

US 2006/0199281 A1 Sep. 7, 2006

Related U.S. Application Data

(60) Provisional application No. 60/594,006, filed on Mar. 3, 2005.

(51) Int. Cl.
*G01N 33/543* (2006.01)
(52) U.S. Cl. .................. 436/518; 435/7.92; 435/962; 436/74; 436/164; 436/172
(58) Field of Classification Search ............ 435/7.1, 435/7.92; 436/518, 523, 525, 73–84, 164, 436/172
See application file for complete search history.

(56) References Cited

U.S. PATENT DOCUMENTS

| | | | | |
|---|---|---|---|---|
| 5,236,826 A * | 8/1993 | Marshall | ........... | 435/7.92 |
| 6,004,743 A * | 12/1999 | Kenyon et al. | ........... | 435/2 |
| 6,266,459 B1 * | 7/2001 | Walt et al. | ........... | 385/12 |
| 6,548,264 B1 * | 4/2003 | Tan et al. | ........... | 435/7.21 |
| 6,649,414 B1 | 11/2003 | Chandler | | |
| 6,803,202 B2 * | 10/2004 | Sullivan et al. | ........... | 435/7.92 |
| 7,129,093 B2 * | 10/2006 | McCleskey et al. | ........... | 436/79 |
| 2004/0058384 A1 | 3/2004 | Bakker et al. | | |
| 2004/0067503 A1 | 4/2004 | Tan et al. | | |
| 2006/0024833 A1 * | 2/2006 | Gee et al. | ........... | 436/73 |
| 2006/0286379 A1 * | 12/2006 | Gao | ........... | 428/403 |

OTHER PUBLICATIONS

Lebedev et al., A modified spectrofluorimetric method for determination of selenium in blood, Pharmaceutical Journal, vol. 30, No. 10, 1996.*
Zhao et al., A rapid bioassay for single bacterial cell quantitation using bioconjugated nanoparticles, PNAS, vol. 101, No. 42, 2004, pp. 15027-15032.*
Zhao et al, Development of Organic-Dye-Doped Silica Nanoparticles in a Reverse Microemulsion, Advanced Materials, 16, No. 2, Jan. 2004, pp. 173-176.*
Parker, C.A. and Harvey, L.G., "Fluorometric determination of submicrogram amounts of selenium." *Analyst* 86, 54-62 (1961).
P.F. Lott, P. Cukor, G. Moriber, and J. Solga, "2, 3-Diaminonaphthalene as a Reagent for the Determination of Milligram to Submicrogram Amounts of Selenium," Analytical Chemistry, vol. 35, No. 9; 1159-1163 (Aug. 1963).
Holzbecher, J. and Ryan, D.E., The fluorimetric determination of mercury. Analytical Chimica Acta, 64 (1973) 333-336.
Budesinsky, B., and West, T.S., "3,5'-Bis(dicarboxymethyl-aminomethyl)-4,4'-dihydroxy-trans-stilbene as a selective spectrofluorimetric reagent for cadmium." Analyst, 94, 182-188 (1969).
Budesinsky, B., and West, T.S., "1-dicarboxymethylaminomethyl-2-hydroxy-3-naphthoic acid as a sensitive and selective fluorimetric reagent for beryllium, and for lanthanum and lutetium in presence of the other lanthanides." Analytica Chimica Acta, 42 (1968) 455-465.
D.F.H. Wallach, D.M. Surgenor, J. Soderberg, and E. Delano, "Preparation and Properties of 3, 6-Dihydroxy-2,4-bis-[N,N'-di-(carboxymethyl)-aminomethyl] fluoran." Analytical Chemistry, vol. 31, No. 3; 456-460 (Mar. 1959).
Extended European Search Report and Written Opinion for corresponding foreign application No. 06748283.6-2401/11861710 PCT/US2006/007611.
Jayaraman et al., Noninvasive in vivo fluorescence measurement of airway-surface liquid depth, salt concentration and pH, The Journal of Clinical Investigation, vol. 107, No. 3, Feb. 2001.
Extended European Search Report and Written Opinion for corresponding foreign application No. 06748283.6-2401/11861710 PCT/US2006/007611, Jun. 25, 2008.

* cited by examiner

*Primary Examiner*—Gailene R Gabel
*Assistant Examiner*—Gary W Counts
(74) *Attorney, Agent, or Firm*—Kinney & Lange, P.A.

(57) ABSTRACT

Surfaces coated with a target-induced fluorescent compound are used to detect target elements, especially trace elements. The target-induced fluorescent compound does not fluoresce when excited at a specific wavelength until it has bound a target element. The use of these coated surfaces provides several benefits including reduced background for greater sensitivity and eliminating the need to separate target-induced fluorescent compound that has not bound target element from target-induced fluorescent compound that has bound target element. Coated nanoparticles are especially useful for detection of target elements.

11 Claims, 4 Drawing Sheets

SURFACES COATED WITH TARGET-INDUCED FLUORESCENT COMPOUNDS FOR DETECTION OF TARGET ELEMENTS

This application claims priority from U.S. Provisional Application No. 60/594,006 filed Mar. 3, 2005 for TARGET-INDUCED FLUORESCENT NANOPARTICLES FOR DETECTION OF TRACE ELEMENTS, which is incorporated by reference.

This invention was made with Government support under Grant No. CHE-0616878, awarded by the National Science Foundation. The Government has certain rights in this invention.

BACKGROUND OF THE INVENTION

The present invention relates to a method and device for detecting target elements. In particular, the present invention relates to surfaces coated with target-specific compounds which produce a detectable signal when bound to the specific target.

A sensitive and rapid detection of trace amounts of toxic elements remains a highly desired objective in providing better human health related to dietary consumption and ingestion derived from agriculture and related food industries. The use of selective and sensitive fluorescent sensory systems for such applications has attracted considerable attention. For example, optical chemosensors with a built-in fluorescence transduction mechanism capable of recognizing specific analytes or target elements in a complex sample matrix have been rationally designed and executed. Both non-ionic and ionic analytes such as sugars, citrate, metal ions, amino acids, creatinine, tripeptides and proteins have been selectively targeted with designed fluorescent compounds.

Recently developed nanoparticle technology possesses a unique feature of higher surface to volume ratio, which affords a significant signal enhancement for detection of biological molecules when the nanoparticles are used as fluorescent signaling reagents in solution (Chandler and Chandler, U.S. Pat. No. 6,649,414; Tan et al, U.S. 2004/0067503 A1). These nanoparticles can be incorporated with a large number of dye molecules to enhance the emission of strong fluorescence signals. However, the fluorescent nanoparticles described in the literature to date have only been used in solution reactions that require separation of the nanoparticles before detection to remove those non-reacted fluorescent nanoparticles. Further, in comparison with the chemical sensors in which detection occurs with a solid sensing platform, the sensitivity using nanoparticles is substantially slower. Therefore, it would be of considerable benefit to devise a detection method that provides increased sensitivity of nanoparticles without requiring additional processing steps or time for binding or separation. The invention described herein is able to resolve both of these limitations in the rapid analysis of trace elements important in human health.

BRIEF SUMMARY OF THE INVENTION

The present invention described herein is a method used for the direct detection of a target element, usually a trace element, in a sample using a surface coated with a target-induced fluorescent compound. After incubating a sample containing an unknown amount of a target element with the coated surface, the linked target-induced fluorescent compound binds the target element. After binding, the complex of element bound to the target-induced fluorescent compound, upon excitation at an appropriate wavelength, will fluoresce at a specific wavelength. The target-induced fluorescent compound that is not bound to a target element is not fluorescent at the specified wavelength. In one embodiment of the invention, each target-induced fluorescent compound recognizes a single predominant target element, and typically, only a single target element.

In a first aspect of the invention, the method for the direct detection of a target element uses a surface that is linked to a target-induced fluorescent compound. The attached target-induced fluorescent compound binds to the target element thereby changing its properties whereby excitation at a specific wavelength causes an emission at a second wavelength. In the absence of a target element, the compound remains inactive at the emission wavelength.

In a second aspect of the invention, the coated surface is any surface that is used to detect emission induced by the target. The coated surface typically comprises a nanoparticle, which may be bound to a second surface that may be flat, spherical or have any other shape.

In a third aspect of the invention, the target is a trace element which includes, but is not limited to, mercury, beryllium, cadmium, chromium, zinc, lead, iron, magnesium, sodium, selenium, and potassium.

In a fourth aspect of the invention, a target-induced fluorescent compound is an organic compound that remains emission inactive unless the compound binds to a target element. Examples of exemplary organic compounds include 2,3-diaminonaphthalene, 3,3,'-diaminobenzidine, 4-[Bis(carboxymethyl)aminomethyl]-3-hydroxy-2-naphthoic acid, 3,3'-[vinylenebis[(6-hydroxy-m-phenylene)methylenenitrilo]]tetra-, E-(8CI), 8-amino-3,7,-dimethyl-10-phenyl-10H-phenazion-2-ylidene ammonium ion and NMBDA.

In a fifth aspect of the invention, a method for the simultaneous direct detection of two or more target elements is prepared using a coated surface that contains two or more target-induced fluorescent compounds where each compound binds a distinct predominant element and each compound is excited by a distinct wavelength and emits at distinct wavelength.

A sixth aspect of the invention is a method for the direct detection of a target element using a nanoparticle that contains target-induced fluorescent compound within the interior of the nanoparticle in an aqueous environment. The target element passes through the nanoparticle shell which encapsulates the aqueous target-induced fluorescent compound whereby the compound binds to the target element thereby changing its properties. Excitation of the target-compound complex at a preferred wavelength causes an emission at a second wavelength. In the absence of a target element the compound remains inactive at the emission wavelength.

In a seventh aspect of the invention, a method for the direct detection of one or more target elements using a nanoparticle whereby the one or more target-induced fluorescent compounds are contained on the surface and within the interior of the particle.

An eighth aspect of the invention is a method for directing of a target-induced fluorescent compound linked to a nanoparticle to a specific microenvironment for the detection of a target element whereby the nanoparticle surface contains a binding moiety such as an antibody, receptor, ligand or like binding molecules that recognizes the specific microenvironment.

In a ninth aspect of the invention, a method for the elimination of an interfering metal or biological molecule on a target-induced fluorescent compound whereby the surface of a nanoparticle contains binding or capture molecules that bind to the interfering metal or biological molecule and the metal to be detected passes through the nanoparticle shell, which encapsulates the aqueous target-induced fluorescent compound. The target-induced fluorescent compound binds to the target element thereby changing its properties whereby upon excitation at a preferred wavelength causes an emission at a second wavelength.

In a last aspect of the invention, a sensor is any surface that is composed of one or more target-induced fluorescent compounds is used to detect one or more target elements. Preferably, the sensor surface consists of nanoparticles recognizing one or more target elements.

DETAILED DESCRIPTION

In the present invention it is advantageous to utilize nanoparticles having high surface to volume ratio that also reduce problems presented by molecules or dyes with intrinsic fluorescence imbued within the nanoparticle structure. By substituting the fluorescent dyes with other substances without the inherent limitations of requiring separation, it was envisioned that a novel nanoparticle sensor for target elements, such as selenium, can be designed for the next generation of nanoparticle-based technology. The invention described herein uses a unique class of organic compounds that behave like switches that are normally non-fluorescent (i.e., non-emissive) when target molecules are absent. However, when these organic molecules bind to the target molecules and form target-compound complexes, they undergo a chemical transition into fluorescent state, thus producing a detectable emission. Unlike nanoparticles containing fluorescent active molecules, target-induced fluorescent compounds incorporated into a nanoparticle do not require a separation procedure to remove those fluorescent compounds not bound to the target elements. A second unique aspect of this invention is that the background signal is reduced, thus avoiding false positives or obscuring low signal levels. Accordingly, an appreciable detectable fluorescent signal is derived from the target element in the sample, which becomes bound to the inducible fluorescent compounds.

In a further improvement, although the sensor chip platform is still two dimensional, spherical nanoparticles used in conjunction with a sensor chip provide significantly larger surface area in which to capture target elements and improve detection sensitivity dramatically. This feature makes the nanoparticle sensor an extremely useful and powerful analytical tool in a variety of applications. In addition, these systems have application in the monitoring of real-time reaction processes and the detection of targets in living system.

"Sensor" means any surface having any shape that is coated with one or more target-induced fluorescent compounds.

"Target" means any element to be detected, usually a trace element.

"Target-induced fluorescent compound" means any organic compound that emits a fluorescent signal after binding to a target element and being excited by an appropriate wavelength.

"Trace element" means any trace element whose abundance in any liquid or solid biological or environment sample to be tested is less than 1 microgram per milliliter or gram of sample.

"Capture molecule or compound" includes antibodies, antigens, ligands, receptors, nucleotides, peptides, proteins, lectin, enzymes, substrates, biochemical and molecular binders, or fragments thereof or any like binding biological or chemical molecules.

The target-induced fluorescent compound is able to bind to a predominant target element, preferably to a single target element and more preferably, to single species of the target element and form target-compound complexes. Target elements include, but are not limited to, mercury, cadmium, zinc, lead, iron, magnesium, sodium, selenium, and potassium. Target-induced fluorescent compounds are organic compounds that include, but are not limited to, 2,3-diaminonaphthalene (DAN) and 3,3,'-diaminobenzidine (DAB) that preferentially bind selenium. For example, DAB has a 580 nm emission in toluene (excitation 420 nm) or a 530 nm emission wavelength (excitation 420 nm) in iso-propanol. The DAB-linked nanoparticles can detect selenium concentrations as low as 15 ppb.

As an illustrative example, the presence of inorganic selenium can be determined by a strong emission signal produced from a reaction of dissolved DAN with aqueous selenite ($SeO_3^{2-}$).

selenite+2,3-diaminonaphthalene→4,5-benzopizaselenol+UV light (366 nm)

This compound, DAN, is a commercially available ortho-diaminophenylene compound that not only captures traces of aqueous $SeO_3^{2-}$, but the 4,5-benzopiaselenol formed in the reaction produces an emission signal that is directly proportional to the selenium concentration in the solution.

Figure 1:
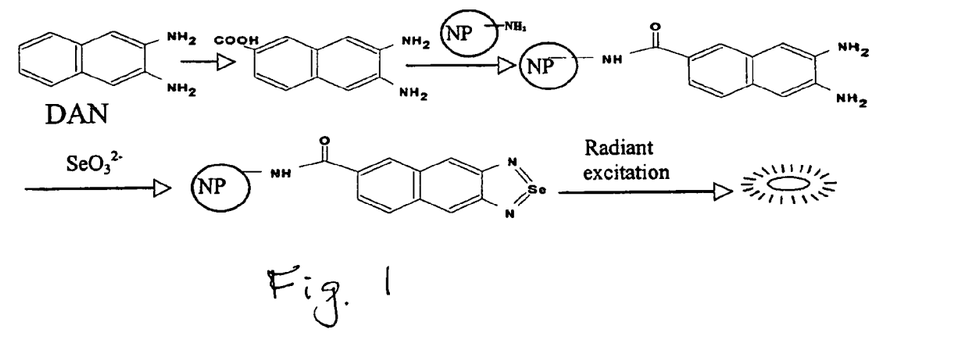
FIG. 1 schematically shows a representative embodiment of the formation of a nanoparticle for detection of selenium.

DAN can be covalently bound to a nanoparticle to form a linked target-induced fluorescent compound and used to detect target elements such as trace amounts of selenium. FIG. 1 shows the covalent linkage of DAN to a nanoparticle and subsequent attachment to selenium. Through known methods, a carboxyl group is added to DAN, which is then incubated with an amine-modified nanoparticle. The carboxyl and amine groups react to form a covalent attachment. In the presence of selenite, 4,5-benzopizaselenol is formed and when excited at the appropriate wavelength, emits a detectable fluorescent signal.

Figure 2:
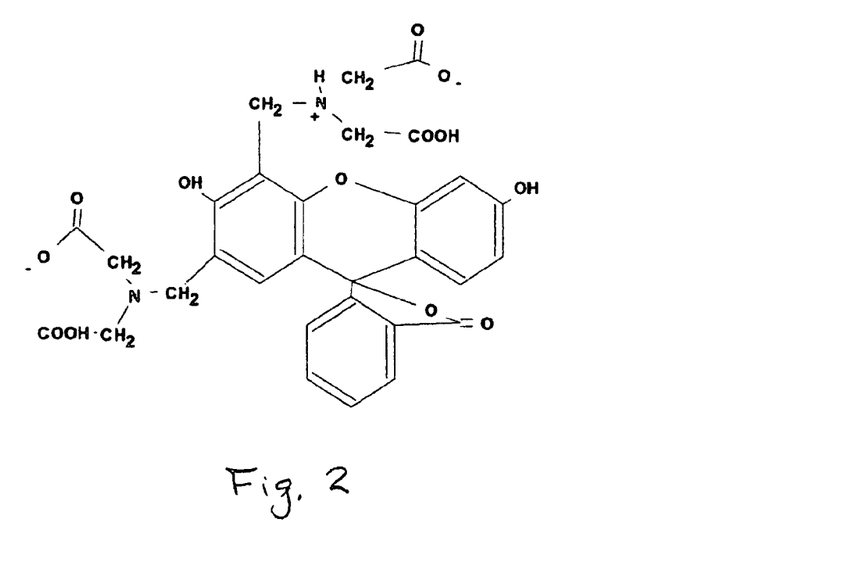
FIG. 2 is a molecular model of NMBDA.

Other target-induced fluorescent compounds that bind preferentially to single target elements are incorporated by example, and not meant to be limitations of the invention, and include 4-[bis(carboxymethyl)-aminomethyl]-3-hydroxy-2-naphthoic acid (DHNA) to detect $Be^{2+}$ (excitation 360 nm, emission 450 nm), acetic acid, 3,3'-[vinylenebis[(6-hydroxy-m-phenylene)methylenenitrilo]]tetra-, E-(8CI) (BDDS) to detect $Cd^{2+}$ (excitation at 440 nm, emission at 360 nm), 8-amino-3,7,-dimethyl-10-phenyl-10H-phenazion-2-ylidene ammonium ion to detect Cr (VI) (excitation 515 nm, emission 560 nm), 3-[(4-amino-2-methyl-5-pyrimidinyl)methyl]-5-(2-hydroxyethyl)-4-methylthiazolium (thiamine) to detect $Hg^{2+}$ (excitation wavelength 370 nm, emission wavelength 440 nm) and NMBDA, shown in FIG. 2, to detect $Ca^{2+}$ (excitation wavelength UV, emission wavelength 490).

Example 1

Synthesis of Functional Nanoparticles Coated with a Target-Induced Fluorescent Compound As a demonstration of the invention for any surface, silica nanoparticles were synthesized using a reverse microemulsion method reported by Tan et al (U.S. 2004/0067503 A1). The diameter of nanoparticles can range from about 1 nm to about 100,000 nm or larger in size, but typically range between about 100 nm to about 2000 nm in size. The nanoparticle may be either solid or porous. The nanoparticle cores are coated with silica using a silicating agent such as tetraethylorthosilicate or trimethylsilylpropyldiethylenetriamine. The surface of silica nanoparticles can be subsequently conjugated with any functional groups that contain either —COOH or —$NH_2$. As one example, cyanogen bromide can be used to covalently couple target-induced fluorescent compounds such as diaminobenzidine through its amino group to the activated nanoparticle.

Other nanoparticles described by Chandler and Chandler (U.S. Pat. No. 6,649,414) may be composed of polystyrene or latex or other polymeric materials such as carbohydrate-based polymers, polyaliphatic alcohols, polyvinyl polymers, polyacrylic acid, polyorganic acids, polyamino acids, polyethers, polyesters, polyaldehydes, and any other synthesized or naturally occurring polymers or mixtures thereof. These polymers may incorporate magnetic or magnetically responsive metal oxides. Other surface materials include carboxymethyl cellulose and hydroxyethyl cellulose. The surface of the particles may be modified to facilitate covalent binding of the target-induced fluorescent compound with groups such as carbohydrates, esters, alcohols, carbamides, aldehydes, amines, sulfur oxides, nitrogen oxides, or halides.

As an illustrative example, the following procedure was used for the synthesis of selective nanoparticles for the detection of selenium. The method can be adopted for synthesis of other specific nanoparticles for detection of different elements based on the similar principle.

Figure 3:
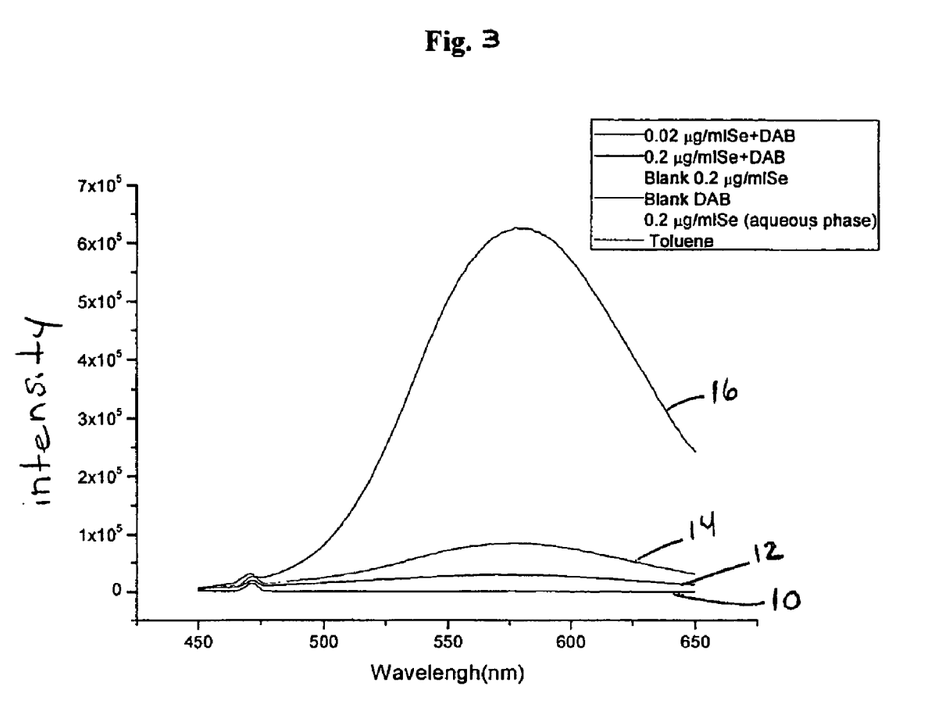
FIG. 3 is emission spectra of DAB in Solution with and without Selenium.

As shown in FIG. 3, it was first demonstrated that upon incubating selenium with a DAB solution, the fluorescence intensity increased with the higher selenium concentration. The fluorescence intensities of various samples were determined at wavelengths between 450 nm and 650 nm. Spectrum 10 is a toluene control, spectrum 12 represents blanks of DAB or selenium, spectrum 14 is a sample containing 0.02 µg/ml selenium+DAB in toluene and spectrum 16 is a sample containing 0.2 µg/ml selenium+DAB in toluene.

A test was subsequently run using nanoparticles. For the production of DAB nanoparticles, 10 mg of silica nanoparticles of 50-90 nm in diameter, with carboxyl functional groups on the surface were activated using 5 ml of 100 mg/ml of 1-ethyl-3-3(3-dimethylaminopropyl) carbodiimide hydrochloride (EDC) and 5 ml of 100 mg/ml of N-hydroxy-succinimide (NHS) in an morpholineethanesulfonic acid (MES) buffer, pH 6.8, for 25 minutes at room temperature with continuous stirring. The nanoparticles were washed with water to remove excess reagents and dispersed in 10 ml of 0.1 M phosphate buffered saline, pH 7.3. To covalently immobilize 3,3-diaminobenzidine (DAB) to the nanoparticle surface, 0.02 mg/ml DAB was reacted with nanoparticles at room temperate for 30 min at pH 6 in MES buffer with continuous stirring, which linked the amine groups of DAB to the carboxyl groups on nanoparticle surface. After thoroughly washing with PBS buffer, the nanoparticles were filtered using a filter membrane with a pore size of about 50 nm, and the DAB nanoparticles are collected.

To demonstrate that the nanoparticles were functional, DAB nanoparticles were incubated with a selenium sample for 2 hours in pH 6 solution at room temperate. After incubation, the particles were microcentrifuged and washed in water. The DAB nanoparticles were resuspended in iso-propanol and their fluorescent emission was detected at 530 nm after excitation at 420 nm using a fluorometer. In Table I, the fluorescence emissions of two concentrations of selenium are shown after the background was subtracted. These results demonstrated the DAB nanoparticles are functionally active, and the amount of fluorescence emission is correlated to the concentration of selenium in the sample.

TABLE I

| Detection of Selenium using DAB Nanoparticles | |
|---|---|
| Samples | Fluorescence Emission Intensity |
| NP-DAB + 0.2 µg/mL Se | 1140 |
| NP-DAB + 2.0 µg/mL Se | 3507 |

Surprisingly, a key feature of this invention was to identify those organic compounds that fluoresce upon binding the target elements and are able to be covalently cross-linked to nanoparticles without hindering binding to target molecules or significantly reducing their fluorescent properties upon binding target elements. These target-induced fluorescent compounds may be coupled to a variety of solid surfaces for the detection of target elements. Solid surfaces are not limited to nanoparticles and may include any and all surfaces to which the target-induced fluorescent compound is linked without significant loss of target-induced fluorescence. For example, target-induced fluorescent compounds may be attached to an antibody which can then, in turn, be attached to a specific antigen that is bound to a surface. Thus, the present invention provides a method for carrying out sensitive biodetection assays in vitro, in vivo or in situ, which is discussed in more detail below.

Example 2

Fabrication of a Sensor Chip

Figure 4:
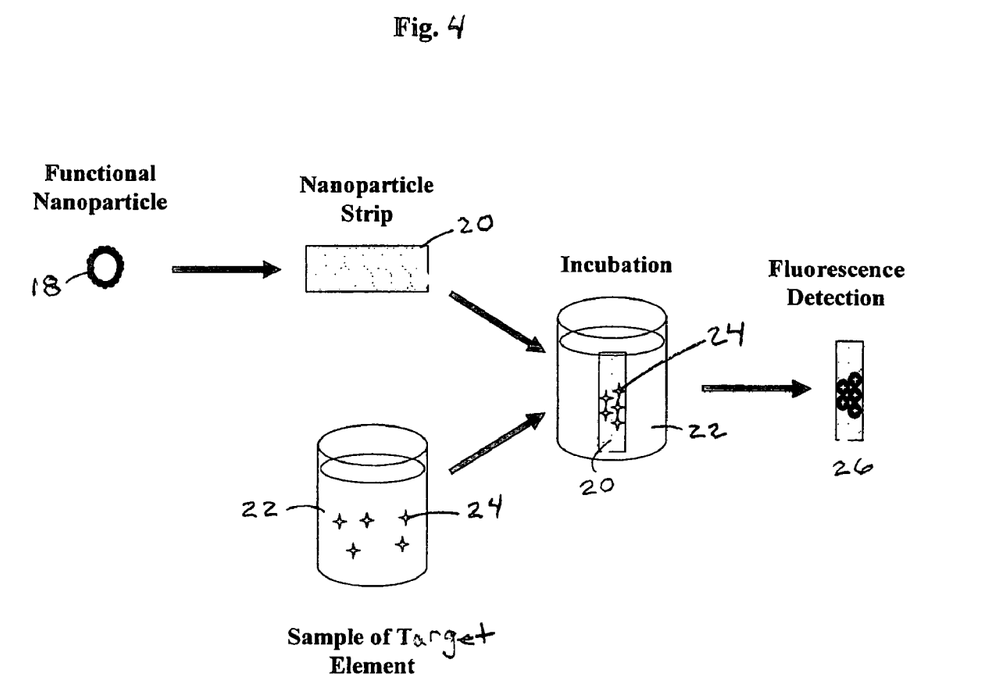
FIG. 4 schematically shows of nanoparticle strip fabrication and detection of a target trace element.

FIG. 4 shows a schematic of an exemplary embodiment of the fabrication and use of a target-induced fluorescent compound nanoparticle strip for the detection of a target element. A suitable functional nanoparticle 18 of the invention contains a covalently bound target-induced fluorescent compound (TIFC) which retains its functional attributes. TIFC nanoparticles are coupled to a detection strip 20, which, in one such example, is a glass slide treated with silica. Detection strip 20 containing a multitude of nanoparticles is incubated in sample solution 22 containing an unknown amount of target element 24. After incubation for a sufficient period of time to bind all of target element 24, detection strip 12 containing target element 24 is washed and is subjected to fluorescence detection 26 at the appropriate wavelengths using a fluorometer.

As a specific illustration, a glass slide pretreated with silica is covered by covalently immobilizing 3,3-diaminobenzidine (DAB) nanoparticles to the glass slide. The three dimensional and open-pore structure afforded by immobilized nanoparticles provides a very high surface density of DAB to which selenium can bind. Selenium is concentrated on the strip surface by incubating the strip for an appropriate period of time. For example, the DAB nanoparticle slide (NP-DAB chip) can be incubated with sample for 2 hours in pH 6 solution at room temperature or alternatively for 20 min at 50° C.

After the selenium is captured on to the NP-DAB chip, the chip is suspended in a toluene or iso-propanol solution in a fluorometer cell. Light of the appropriate wavelength is shown through the cell resulting in the NP-DAB-Se complexes emitting fluorescent signals at 580 nm in toluene (excitation 420 nm) or at 530 nm in iso-propanol (excitation 420 nm), respectively.

Example 3

Simultaneous Detection of Two or More Target Elements with Different Nanoparticles A further utility of the present invention is the simultaneous detection of two or more target elements. Because target-induced fluorescent compounds may contain different excitation and emission properties, two or more target elements may be simultaneously detected using a coated surface containing two or more target-induced fluorescent compounds. For example, a dual target-induced fluorescent sensor strip is prepared by coating one set of nanoparticles with acetic acid, 3,3'-[vinylenebis[(6-hydroxy-m-phenylene)methylenenitrilo]]tetra-, E-(8CI) (BDDS) and a second set with 3,3,'-diaminobenzidine (DAB). Approximately equal amounts of both nanoparticles are bound to a silica coated glass slide. The coated slide is placed in a sample containing cadmium and selenium and incubated for an appropriate amount of time. BDDS and DAB will bind cadmium and selenium, respectively. After washing the slide, a fluorometer is used to detect the concentrations of cadmium and selenium at 360 nm (excitation at 440 nm) and 580 nm (excitation at 420 nm), respectively.

Example 4

Doping Target-Induced Fluorescent Compounds Inside Nanoparticles

In another representative embodiment, target-induced fluorescent compounds are coated on the inside of a nanoparticle, such as a silica matrix. Uniform and well-dispersed Zn-induced fluorescent silica nanoparticles were synthesized using a reverse microemulsion method and carboxymethyl-[4-[10-(4-dicarboxymethylaminobenzyl)anthracen-9-ylmethyl]phenyl]amino) acetic acid dipotassium salt (CDAPAP) molecules were doped inside nanoparticles.

A microemulsion was formed with 1.77 mL of surfactant (Triton X-100), 0.48 mL of 2 mM CDAPA in pH 3 HCl solution (to increase positive charges) and 9.30 mL of oil (hexanol+cyclohexane). After 20 min of stirring, 50 µL of tetraethoxysilane (TEOS) was added to the microemulsion. Polymerization was initiated by adding 60 µL of $NH_4OH$ to the microemulsion. After continuous stirring for 24 hours, 50 µL of TEOS and 50 µL of N-(trimethyl-oxysilylpropyl)-ethylere diamine triacetic acid trisodium salt were added to the microemulsion to form —COOH groups on the nanoparticle surfaces. After another 24 hours of stirring, silica nanoparticles with internally doped CDAPAP were obtained having diameters of about 50±3 nm.

In order to trap target-induced fluorescent compounds inside a silica matrix, the target-induced fluorescent compounds are typically hydrophilic and have a stabilizing structure, state or charge. The polymerization of TEOS takes place in the water pool of the microemulsion and results in the formation of the silica matrix of the nanoparticles. Thus, to trap functional molecules inside the silica matrix they should be able to remain in the water pool rather than in the oil phase of the microemulsion.

The target-induced fluorescent compounds should also essentially remain inside the nanoparticles to obtain accurate and reproducible measurements of target concentrations. Therefore, target-induced fluorescent compounds used in these applications typically allow either physical or chemical entrapment within the silica matrix. Chemical entrapment can include forming chemical bonds between the compounds and the silica matrix, while physical entrapment can include using effects of size, physical state, or charge of the compounds relative to the silica matrix. Large molecules remain trapped, because they cannot pass through the pores of the silica matrix. Solid state molecules remain trapped because of slow mass-transport. Charged molecules remain trapped because of an effective electrostatic attraction force between the compounds and the silica matrix. Because the silica matrix is negatively charged, positively charged molecules can be retained inside the silica matrix.

Nanoparticles that contain one or more target-induced fluorescent compounds within an aqueous interior can be modified on the cell surface to contain a variety of properties to enhance or alter their detection properties. For example, the surface can be bound to one or more target-induced fluorescent compounds that are the same as those within the aqueous interior to enhance the signal. Or the surface can be bound to one or more target-induced fluorescent compounds that are distinct from target-induced fluorescent compounds within the aqueous interior to detect additional elements. Alternatively, the surface of the nanoparticle can be covalently bound to a capture molecule or compound that is able to bind to a unique site on a specific microenvironment, such as a cell, tissue or the like, for the detection of a target element in the microenvironment. A capture binding moiety may include antibodies, antigens, ligands, receptors, nucleotides, peptides, proteins, lectin, enzymes, substrates, biochemical and molecular binders, or fragments thereof or any like binding biological or chemical molecules. In yet other examples, the surface can contain covalently bound biological or chemical molecules that bind to elements that may interfere with a target-induced fluorescent compound in the detection of a specific target element or a valence state of that element.

In an illustrative example, a capture particle may be attached to the outer surface of a nanoparticle, which has an inner surface coated with a target-induced fluorescent compound as described above. For example, CDAPAP is a target-induced fluorescent compound that is induced by either $Cd^{2+}$ or $Zn^{2+}$. A sample may contain both target elements, but the detection of only $Zn^{2+}$, for instance, may be desired. In this circumstance, the outer surface of the CDAPAP-doped nanoparticle may be coated with a $Cd^{2+}$-specific capture particle. The $Cd^{2+}$-specific capture particle will capture and trap $Cd^{2+}$ to prevent it from reaching the CDAPAP within the nanoparticle. The result is induction of fluorescence essentially only by $Zn^{2+}$. Any particle or molecule that is attachable to the nanoparticle surface and able to trap or capture potentially interfering target elements may be utilized.

Example 5

Simultaneous Detection of Zinc and Selenium Using the Same Nanoparticles Coated with CDAPAP on the Inner Surface and DAB on the Outer Surface In another representative embodiment, nanoparticles were doped with CDAPAP on the inner surfaces and coated with DAB on the outer surfaces as described above. The resulting nanoparticles were incubated in samples containing zinc, selenium or both targets, and fluorescence was detected in a fluorometer.

Figure 5:
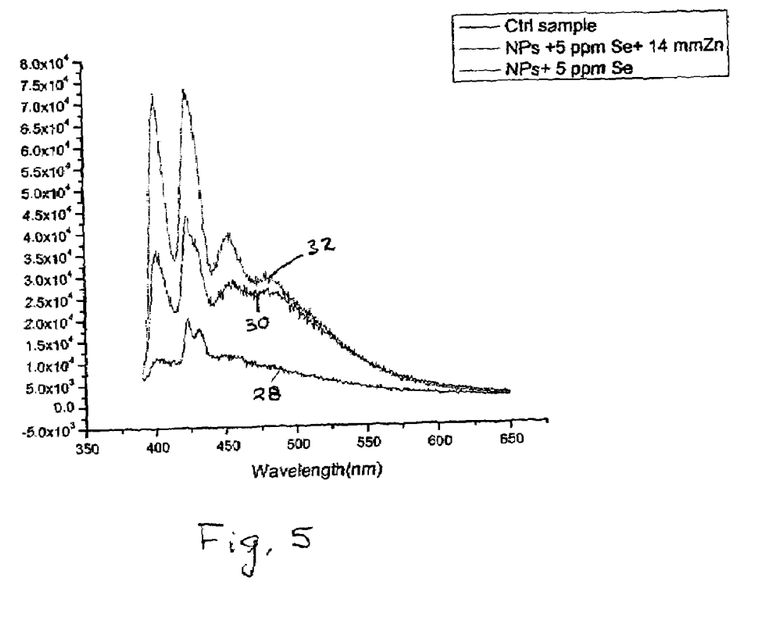
FIG. 5 is emission spectra of CDAPAP/DAB nanoparticles for detection of zinc.

FIG. 5 shows resulting fluorescence spectra for zinc detection using an excitation wavelength of 377 nm. Spectrum 28 is a control sample, spectrum 30 is a sample containing nanoparticles+5 ppm selenium and spectrum 32 is a sample containing nanoparticles+5 ppm selenium+14 mM zinc. As evident from the spectra, the zinc was detectable in the sample.

Figure 6:
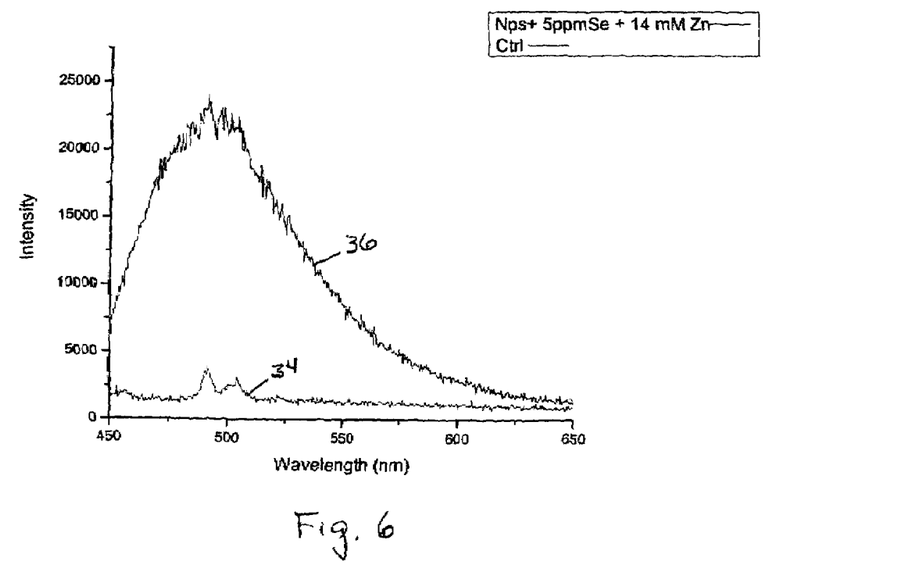
FIG. 6 is emission spectra of CDAPAP/DAB nanoparticles for detection of selenium.

FIG. 6 shows resulting fluorescence spectra for selenium detection using an excitation wavelength of 430 nm. Spectrum 34 is a control sample and spectrum 36 is a sample containing nanoparticles+5 ppm selenium+14 mM zinc. The spectra show that selenium was detectable in the sample.

The surfaces coated with target-induced fluorescent compounds of the present invention provide several benefits in the analysis and detection of target elements, especially trace elements. First, the proposed coated surfaces will be able to specifically recognize and enrich trace amounts of target elements. Thus, the surfaces will become a concentrated fluorescence source to provide an enhanced and more detectable signal. It is beneficial to employ small surfaces, such as nanoparticles, as a substrate for increased mobility and surface area. High surface area to volume ratio is one of the major features of nanomaterials. As the size of the nanoparticles decreases, the surface area to volume ratio increases. This property allows more of the compounds to be exposed to the target elements.

The small size also makes the nanoparticles highly mobile, which enables them to easily reach target elements within various matrices, such as eukaryotic or prokaryotic cells. Therefore, a higher number of the target elements can be captured within a smaller volume sample, yielding a concentrated target element center in the matrix.

Second, most of the fluorescent nanomaterials used in analysis today have intrinsic fluorescence and cannot be used for target-induced applications. The coated surfaces described here do not contain any dye molecules, thus, no permanent fluorescence exists. Rather, the coated surfaces contain specific compounds that can only become fluorescent when activated through binding to target elements. Any detectable fluorescence signals will come when targets are captured from a sample. The switch-like property of the compounds can indicate in situ the presence of the target elements. Moreover, the target-induced signal results in reduced fluorescence background signal, which reduces false positive readings and enables detection of low signal levels.

Third, separation of unbound intrinsically fluorescent nanomaterials from the complexes of target-nanomaterials is complicated and time consuming, yet necessary for most detection methods using fluorescent labeling reagents. The coated surfaces described here provide a small reaction center with plenty of target-induced fluorescent compound to selectively bind to target elements. Because the unbound compound will not be fluorescent, there is no need for separation, thereby making the detection simple and rapid.

Fourth, the proposed coated surfaces provide a unique opportunity to study in situ the characteristics of chemical binding at nanoscale surfaces. As the chemical binding proceeds, it can be easily monitored by the switchable nature of the fluorescence output. For example, it can be used to monitor $Cd^{2+}$ binding processes in cells to study $Cd^{2+}$ toxicity in living systems. Additionally, by coating inner and outer surfaces of cells with target-induced fluorescent compounds, the transport of various target elements may be monitored.

The coated surfaces can also monitor, in situ, metal ion transport and transformations in the environment. For example, $Hg^{2+}$ is easily transferred to $CH_3Hg^+$ in surface water, such as in rivers, lakes and oceans. $CH_3Hg^+$ is much more toxic than $Hg^{2+}$ and accumulates in fish resulting in major health concerns. The compounds of the coated surfaces are able to "switch off" to indicate that $Hg^{2+}$ has transferred to $CH_3Hg^+$. Accordingly, the coated surfaces will serve as probes to kinetically monitor reaction processes through fluorescence signal changes occurring within nanoscale domains.

The coated surfaces may be extended to biochemical and toxic organic targets for applications ranging from environmental monitoring to national security. These include cellular-level biochemical markers for bacteria and airborne toxin markers for chemical warfare releases.

The description of the specific embodiments of the invention is presented for the purpose of illustration. It is not intended to be exhaustive or to limit the scope of the invention to the specific forms described herein. Although the invention has been described with reference to several embodiments, it will be understood by one of ordinary skill in the art that various modifications can be made without departing from the spirit and the scope of the invention, as set forth in the claims. Other embodiments are within the claims. All patents, patent applications and publications referenced herein are hereby incorporated by reference.

The invention claimed is:

1. A method for direct detection of a trace element, the method comprising:
   (a) linking a surface of a nanoparticle with a compound to form a nanoparticle-linked compound, wherein the compound is selected from a group consisting of:
   2,3-diaminonapthalene (DAN);
   3,3,'-diaminobenzidine (DAB);
   4-[bis(carboxymethyl)-aminomethyl]-3-hydroxy-2-naphthoic acid (DHNA);
   acetic acid, 3,3'-[vinylenebis[(6-hydroxy-m-phenylene)methylenenitrilo]]tetra-, E-(8CI) (BDDS);
   8-amino-3,7,-dimethyl-10-phenyl-10H-phenazion-2-ylidene ammonium ion;
   3-[(4-amino-2-methyl-5-pyrimidinyl)methyl]-5-(2-hydroxyethyl)-4-methylthiazolium (thiamine);
   carboxymethyl-[4-[10-(4-dicarboxymethylaminobenzyl)anthracen-9-ylmethyl]phenyl]amino) acetic acid dipotassium salt (CDAPAP); and
   NMBDA, wherein NMBDA is a compound of the formula:

(b) incubating a sample containing the trace element with the nanoparticle-linked compound for a time sufficient to bind the trace element to the nanoparticle-linked compound to form a trace element bound nanoparticle-linked compound, wherein the trace element is selected from a group consisting of selenium, beryllium, cadmium, chromium, mercury, zinc, and calcium, and wherein the trace element bound nanoparticle-linked compound is selected from a group consisting of:

nanoparticle-linked 2,3-diaminonapthalene (DAN) bound to selenium;

nanoparticle-linked 3,3,'-diaminobenzidine (DAB) bound to selenium;

nanoparticle-linked 4-[bis(carboxymethyl)-aminomethyl]-3-hydroxy-2-naphthoic acid (DHNA) bound to beryllium;

nanoparticle-linked acetic acid, 3,3'-[vinylenebis[(6-hydroxy-m-phenylene)methylenenitrilo]]tetra-, E-(8CI) (BDDS) bound to cadmium;

nanoparticle-linked 8-amino-3,7,-dimethyl-10-phenyl-10H-phenazion-2-ylidene ammonium ion bound to chromium;

nanoparticle-linked 3-[(4-amino-2-methyl-5-pyrimidinyl)methyl]-5-(2-hydroxyethyl)-4-methylthiazolium (thiamine) bound to mercury;

nanoparticle-linked carboxymethyl-[4-[10-(4-dicarboxymethylaminobenzyl)anthracen-9-ylmethyl]phenyl]amino) acetic acid dipotassium salt (CDAPAP) bound to zinc; and nanoparticle-linked NMBDA bound to calcium, wherein NMBDA is a compound of the formula:

(c) exposing the trace element bound nanoparticle-linked compound to light having a wavelength that excites the trace element bound nanoparticle-linked compound; and (d) detecting a fluorescent signal emitted by the trace element bound nanoparticle-linked compound.

2. The method of claim 1, wherein the surface is an outer surface of the nanoparticle.

3. The method of claim 1, wherein a diameter of the nanoparticle measures between about 1 nanometer and about 100,000 nanometers.

4. The method of claim 1, further comprising linking the nanoparticle to a substrate to form a nanoparticle sensor.

5. The method of claim 1, further comprising attaching a capture compound to the surface of the nanoparticle.

6. The method of claim 5, wherein the capture compound comprises biochemical or molecular binding entities, selected from a group consisting of antibodies, antigens, ligands, receptors, nucleotides, peptides, proteins, lectin, enzymes, substrates, or fragments thereof.

7. The method of claim 5, wherein the capture compound captures a binding site on a surface of a cell or tissue.

8. A method for direct detection of a trace element in the presence of an interfering element to produce a desired fluorescent signal, the method comprising:

(a) forming a nanoparticle-linked compound, comprising:
(1) forming a microemulsion containing a first compound;
(2) forming a porous nanoparticle from the microemulsion, the first compound being trapped inside the porous nanoparticle, wherein the first compound is selected from a group consisting of:

2,3-diaminonapthalene (DAN) capable of binding selenium;

3,3,'-diaminobenzidine (DAB) capable of binding selenium;

4-[bis(carboxymethyl)-aminomethyl]-3-hydroxy-2-naphthoic acid (DHNA) capable of binding beryllium;

acetic acid, 3,3'-[vinylenebis[(6-hydroxy-m-phenylene)methylenenitrilo]]tetra-, E-(8CI) (BDDS) capable of binding cadmium;

8-amino-3,7,-dimethyl-10-phenyl-10H-phenazion-2-ylidene ammonium ion capable of binding chromium;

3-[(4-amino-2-methyl-5-pyrimidinyl)methyl]-5-(2-hydroxyethyl)-4-methylthiazolium (thiamine) capable of binding mercury;

carboxymethyl-[4-[10-(4-dicarboxymethylaminobenzyl)anthracen-9-ylmethyl]phenyl]amino) acetic acid dipotassium salt (CDAPAP) capable of binding zinc; and NMBDA capable of binding calcium, wherein NMBDA is a compound of the formula:

(3) attaching a second compound on an outer surface of the porous nanoparticle, wherein the second compound is a capture molecule capable of binding the interfering element to prevent the interfering element from binding to the first compound;

(b) incubating a sample containing the trace element and the interfering element with the nanoparticle-linked compound for a time sufficient to bind the trace element to the first compound trapped inside the porous nanoparticle and for the interfering element to bind the second compound attached to the outer surface of the porous nanoparticle to form a trace element bound nanoparticle-linked compound, wherein the trace element is selected from a group consisting of selenium, beryllium, cadmium, chromium, mercury, zinc, and calcium;

(c) exposing the trace element bound nanoparticle-linked compound to light having a wavelength that excites the trace element bound nanoparticle-linked compound; and (d) detecting the desired fluorescent signal emitted by the trace element bound nanoparticle-linked compound.

9. The method of claim 8, wherein a diameter of the porous nanoparticle measures between about 1 nanometer and about 100,000 nanometers.

10. The method of claim 8, further comprising linking the nanoparticle to a substrate to form a nanoparticle sensor.

11. The method of claim 8, wherein the capture compound comprises biochemical or molecular binding entities selected from a group consisting of antibodies, antigens, ligands, receptors, nucleotides, peptides, proteins, lectin, enzymes, substrates, or fragments thereof.

* * * * *